United States Patent [19]

De Giorgio

[11] Patent Number: 5,705,356
[45] Date of Patent: Jan. 6, 1998

[54] REAGENT FOR INVITRO DIAGNOSTIC DETERMINATION OF BICARBONATE

[75] Inventor: Joseph De Giorgio, Clayton, Australia

[73] Assignee: Trace Scientific Limited, Clayton, Australia

[21] Appl. No.: 564,140

[22] PCT Filed: Jul. 13, 1994

[86] PCT No.: PCT/AU94/00392

§ 371 Date: Nov. 29, 1995

§ 102(e) Date: Nov. 29, 1995

[87] PCT Pub. No.: WO95/07999

PCT Pub. Date: Mar. 23, 1995

[30] Foreign Application Priority Data

Sep. 17, 1993 [AU] Australia .................. PM 1311

[51] Int. Cl.$^6$ .................. C12Q 1/26; C12Q 1/32; C12Q 1/54; C12N 1/00
[52] U.S. Cl. .................. 435/25; 435/26; 435/14; 435/4; 435/7.91; 435/832; 435/853; 435/963; 424/94.1; 424/94.3; 424/94.4; 436/63; 436/74
[58] Field of Search .................. 435/25, 26, 7.91, 435/14, 832, 853, 4, 963; 436/63, 74, 815; 424/94.1, 94.3, 94.4

[56] References Cited

U.S. PATENT DOCUMENTS 4,394,449 7/1983 Modrovich .................. 435/188
5,116,728 5/1992 Crowther et al. .................. 435/14

FOREIGN PATENT DOCUMENTS

| 61906/90 | 2/1991 | Australia. |
| 0 076 478 | 4/1983 | European Pat. Off. . |
| 0076478 | 4/1983 | European Pat. Off. . |

*Primary Examiner*—Louise Leary
*Attorney, Agent, or Firm*—Greenlee, Winner and Sullivan PC

[57] ABSTRACT

The invention provides a reagent for enzymatic determination of serum bicarbonate levels in a patient wherein the degree of oxidation of a coenzyme is measured and said reagent is stabilized against oxidation by a coenzyme reduction system comprising an enzyme and substrate pair selected to enable continuous regeneration of said coenzyme throughout storage of said reagent. The invention also provides an improvement in an enzymatic method of determination of the concentration of serum bicarbonate in a sample body fluid wherein the degree of oxidation of a coenzyme is measured, the improvement comprising stabilizing a reagent which comprises the coenzyme against oxidation by a coenzyme reduction system comprising an enzyme and substrate pair selected so as to enable continuous regeneration of the coenzyme throughout storage of the reagent.

23 Claims, No Drawings

REAGENT FOR INVITRO DIAGNOSTIC DETERMINATION OF BICARBONATE

This invention relates to reagents used in enzymatic methods of determining the concentration of serum bicarbonate in a sample body fluid. In particular, this invention relates to reagents used in methods wherein the quantity of an oxidized coenzyme in the reacted sample corresponds directly to the concentration of bicarbonate present in the sample. The invention also relates to improved methods for carrying out the determination of the bicarbonate concentration.

The quantification of analytes, in particular, bicarbonate, in sample body fluids may involve contrasting a sample "blank" against a sample in which an enzymatic conversion of the analyte has taken place.

To achieve enzymatic conversion of the bicarbonate, substrate specific enzymes are allowed to act upon enzyme substrates known for use in quantification of the serum bicarbonate. The change in the reaction composition with respect to the blank can be calculated by various methods measuring the change in absorbance of the composition. The change in absorbance correlates directly to the amount of bicarbonate present in the sample.

Whilst traditional methods including colorimetric determination, partial pressure analysis and electrode testing have proved adequate, enzymatic analysis has been shown to be vastly more accurate, reliable and simpler than these other methods when it comes to the determination of serum bicarbonate levels.

A commonly used method of quantification of total $CO_2$ in a sample requires mixing the patient sample with the substrate phosphoenolpyruvate (PEP). A blank reading may be taken at this point. The substrate specific enzyme, phosphoenolpyruvate carboxylase (PEPC) is then added to the reaction mixture causing the conversion of PEP to oxaloacetate (OAA) and phosphate.

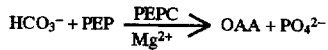

Although various methods may then be undertaken to correlate the oxaloacetate with the total $CO_2$ in the sample the most common methodology requires the coupling of the oxaloacetate with reduced nicotinamide adenine dinucleotide (NADH) and malate dehydrogenase (MDH), the result of this reaction being the oxidation of nicotinamide adenine dinucleotide and the formation of malate.

The resulting concentration of NAD+ correlates to the concentration of total $CO_2$ originally present in the sample.

Historically, enzymatic Bicarbonate reagents have suffered from poor reconstituted stability. The cause of this instability could be attributed both to the deterioration of endogenous ingredients in solution coupled with the reagents uptake of atmospheric $CO_2$. PEPC (phosphoenol pyruvate carboxylase), traditionally sourced from maize leaves, is particularly susceptible to oxidative degradation for example, by endogenous contaminants such as NADH oxidase and proteases which slowly degrade the potency of PEPC. NADH (Nicotinamide-adenine dinucleotide, reduced) will rapidly decompose in solution especially in an acidic medium, although storage of the NADH at an alkaline pH dramatically improves its reconstituted stability.

Most reagents for the determination of serum bicarbonate are formulated at an alkaline pH of approximately 8.0. At this pH, atmospheric $CO_2$ becomes problematic. This exogenous $CO_2$ absorption trigger a sequence of enzymatic reactions resulting in a subsequent loss of NADH and the consequent reduction in absorbance and reagent stability. Reagent reconstitution with poor quality laboratory water has the same detrimental effects as just described.

Reagents thus have a very short effective life even when pampered to reduce exposure to atmospheric $CO_2$.

One means of overcoming this difficulty has been to generate reduced coenzyme in the reagent just prior to its use.

One such method is described in Australian patent application AU-A-61906/90 (02128191) Hoffmann La Roche AG. In this disclosure the reduced coenzyme is generated in situ either simultaneously with or prior to reoxidation of the coenzyme by the analyte, substrate and specific enzymes. This is achieved by including in the reaction mixture an enzyme and enzyme substrate enabling the reduction of the atmospherically oxidized coenzyme. The specific reaction disclosed and favoured by F. Hoffmann La Roche AG is:

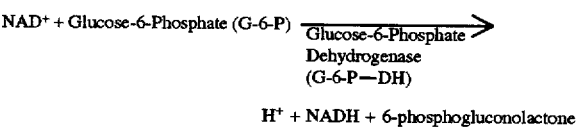

This makes available reduced nicotinamide adenosine dinucleotide.

The problem associated with this mode of generation of NADH is that a stable single vial reagent configuration is not possible.

F. Hoffmann La Roche AG have to a certain extent overcome this problem by dividing the reagent system into 2 vials. The first reagent comprises the substrate specific enzymes; in the case of $CO_2$ quantification, PEPC, MDH and G-6-P-DH, and the second reagent the enzyme substrates and the coenzyme, in the case of $CO_2$ determination, PEP, G-6-P and NAD+ (oxidized state). The determination reaction thus proceeds as follows:

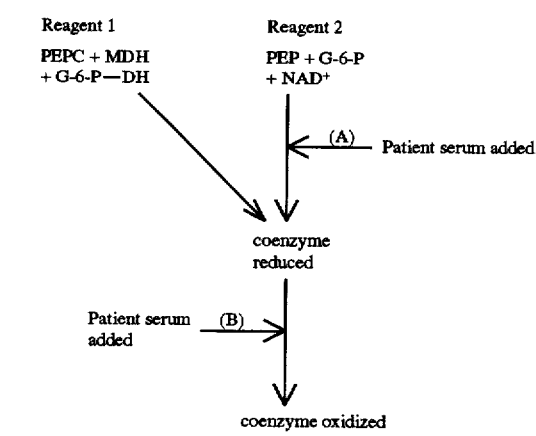

where (A) and (B) represent alternative, equivalent routes.

Difficulties remain, however, with this reagent system. Apart from the fact that two reagent vials are required thus increasing cost, inventory and waste, very accurate levels of glucose-6-phosphate are required and moreover, the system is limited to use in specific chemical analyzers. As soon as the reagents are combined, generation of NADH from NAD+ occurs by exhaustion of glucose-6-phosphate.

Because glucose-6-phosphate is thus exhausted, stability of the combined reagent could be severely affected if the two reagents were to be combined and not immediately used. If inaccurate or excess levels of glucose-6-phosphate are present, the timing associated with incubation of the reagent is critical. Results may be falsely low absorbance changes and grossly inaccurate results.

One earlier solution described in U.S. Pat. No. 4,394,449 (July 1983) to Modrovich uses substrate/enzyme pairs to generate the reduced coenzyme as does the Roche solution, however, in this case Glucose-6-phosphate is generated from Glucose in accordance with the following:

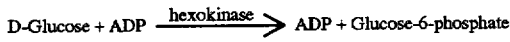

D-Glucose + ADP —hexokinase→ ADP + Glucose-6-phosphate

NAD+ then reacts with the formed Glucose-6-phosphate in the presence of the enzyme Glucose-6-phosphate Dehydrogenase to form NADH. Modrovich also includes both NADH and NAD+ in the formulation such that when NADH is oxidised or destroyed, the NAD+ present in the reagent will aid the regeneration of NADH. This is also a two vial reagent.

A third alternative is provided by Crowther et al in U.S. Pat. No. 5,116,728 (May 1992) In this invention the concept of enzyme/substrate pairs is utilized to regenerate NADH. This invention differs from those of Roche and Modrovich in that the regeneration reaction is slowed down to approximately 2% of the maximum rate by the use of very low levels of enzyme. In addition there is the inclusion of a stabilizer, which in effect is the addition of NAD+, at a theoretically pre-determined level which will set up an equilibrium between NADH and NAD+ and control the rate of generation. Both generation of NADH and regeneration of NADH occur within the system. It is not clear upon which the system is more reliant. The disadvantage of this system is that very low levels of enzyme in solution are very unstable and will affect the long term stability of the reagent. This is evident in the stability claimed for the ALT reagent which is indicated as being 22 days in a refrigerated environment. In addition it is a requirement that the reagent be configured in two parts.

The general problem associated with the NADH generation mechanism adopted by each of the inventions described hereinabove, that is

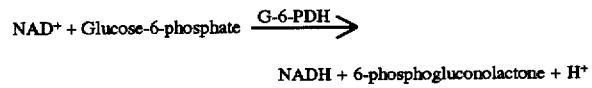

NAD+ + Glucose-6-phosphate —G-6-PDH→

NADH + 6-phosphogluconolactone + H+ is that a single step reaction using a single vial is not possible because as soon as the patient serum is added to the reagent, two simultaneous reactions occur:

(a) a decrease in absorbance due to NADH being converted to NAD+, (b) generation of NADH from NAD+ resulting in an increase in absorbance.

These two reactions occur at similar velocities with the net result being a falsely low absorbance change and grossly inaccurate results.

Accordingly, it is an object of this invention to provide a reagent system for use in determination of serum bicarbonate levels which substantially ameliorates the problems of prior art reagent systems used in enzymatic analysis of serum bicarbonate levels relying on the oxidation of a coenzyme, particularly those problems which relate to endogenous or exogenous contamination of the reagent. It is a further object of this invention to provide an improved method of determination of the concentration of bicarbonate levels in a patient sample, the method overcoming the problems associated with prior art methods including premature oxidation of the coenzyme determinant and the necessity for a multi-vial system to minimize contamination of the reagent.

To this end there is provided a reagent for enzymatic determination of the concentration of serum bicarbonate levels in a patient wherein the degree of oxidation of a coenzyme is measured, characterized in that said reagent is stabilized against oxidation by a coenzyme reduction system comprising an enzyme and substrate pair selected so as to enable continuous regeneration of said coenzyme throughout storage of said reagent.

Preferably, the coenzyme reduction system comprises an enzyme and a substrate, said enzyme having incomplete specificity for said substrate thereby resulting in a reduced rate of cross reactivity.

The reagent is preferably in a single vial configuration.

Throughout this specification the term "incomplete specificity" is used with respect to enzyme and substrate pairs wherein the substrate selected is not the natural substrate of the enzyme selected and thus has less than 100% cross specificity for the enzyme concerned.

This invention is predicated on the discovery that by coupling an enzyme and substrate having incomplete specificity for each other, the rate of coenzyme reduction is considerably slowed. By slowing down the reduction reaction, the essential components of the reagent can be contained within one storage vial, the contents being stabilized against contamination by the low level continuous regeneration of the coenzyme. By slowing down the process, the regeneration of NADH can occur without affecting the measurement of serum bicarbonate. The regeneration can occur in the reagent when not in use and the velocity at which regeneration occurs can be fine tuned by adjusting the nature of the enzyme/substrate pair selected and the levels thereof.

In an alternate embodiment of the invention, there is provided a reagent for use in an enzymatic method of determination of the concentration of serum bicarbonate levels in a patient wherein the degree of oxidation of a coenzyme is measured, characterized in that said reagent is stabilized against oxidation by a coenzyme reduction system comprising an enzyme and substrate pair selected so as to enable regeneration of said coenzyme at a rate of 0.10–0.90 mAbs/min at 20°–25° C.

Preferably the rate of regeneration in a reagent according to this aspect of the invention is 0.20–0.80 mAbs/min at 20°–25° C.

In a preferred embodiment of the invention, the degree of specificity between the substrate and enzyme of the coenzyme reduction system is preferably less than 100%, more preferably less than 50% and most conveniently less than 10% on an equimolar basis. Optimally, an enzyme/substrate pair having a cross-reactivity of less than 5% on an equimolar basis may be used.

The coenzymes preferably used in the reagent according to the invention are reduced nicotinamide adenine dinucleotide (NADH) and reduced nicotinamide adenine dinucleotide phosphate (NADPH) although coenzyme analogs such as nicotinamide hypoxanthine dinucleotide phosphate or thio-NADH may also be suitable.

Enzymes preferably utilised in the coenzyme reduction system for determination of the $CO_2$ content of a serum sample may be glucose-6-phosphate dehydrogenase (G-6-P-DH) or glucose dehydrogenase.

Enzymes such as formate dehydrogenase, glycerol dehydrogenase, leucine dehydrogenase, L-Alanine dehydrogenase, 3α-Hydroxy-steroid Dehydrogenase, L-lactate Dehydrogenase (from Lactobacillus sp.) or Glycerol-3-phosphate dehydrogenase may also be suitable. The preferred enzyme used for total $CO_2$ determination reagents is glucose-6-phosphate dehydrogenase. This may be obtained from any suitable source such as *Leuconostoc mesenteroides*, *Bacillus stearothermophilus*, *Zymomonas mobilus* or yeast.

Such enzymes are preferably derived from microbial sources. The incorporation into the reagent of enzymes from microbial sources has been found to eliminate the presence of endogenous contaminants such as NADH oxidase and proteases which previously severely affected the stability of the reagents. The microbial enzymes also have the added advantage of being more thermostable thereby improving their long term stability in solution.

The more preferred source of glucose-6-phosphate dehydrogenase is from *Leuconostoc mesenteroides*. If glucose-6-phosphate from *Bacillus stearothermophilus* or *Zymomonas mobilus* is used, the rate of reaction is reduced. Similarly, if Yeast is used as the source of glucose-6-phosphate dehydrogenase, the coenzyme NADPH must be used as an alternative to NADH since yeast glucose-6-phosphate dehydrogenase only acts on NADP+.

Bearing in mind that the selection of substrate and enzyme must be such that in the coenzyme reduction system they have incomplete specificity for each other, suitable substrates for use in the reagent according to the invention include Ribose-5-phosphate, Glucose-1-phosphate, 6-phosphogluconic acid, 2-deoxyglucose-6-phosphate, 2-deoxy-2-fluoroglucose-6-phosphate, 2-deoxy-2-chloroglucose-6-phosphate, 2-deoxy-2, 2-difluoroglucose-6-phosphate, 2-O-methylglucose-6-phosphate, mannose-6-phosphate, glucosamine-6-phosphate, 3-deoxyglucose-6-phosphate, 3-deoxy-3-fluoro-glucose-6-phosphate, 3-O-methylglucose-6-phosphate, allose-6-phosphate, ahrose-6-phosphate, 4-deoxy-4-fluoroglucose-6-phosphate, galactose-6-phosphate, 5-thio-glucose-6-phosphate, phosphonate analogs, glucose-6-stallate, β-B-D-glucose, D-galactose, 2-deoxyglucose, arabinose, xylose, 1-sorbose, D-mannose, D-fructose, D-lactose, D-sorbital, D-mannitol, saccarose, inositol, maltose.

Using NAD+ as the preferred coenzyme in the reagent, the preferred enzyme/substrate combination is Glucose-6-phosphate dehydrogenase (G-6-P-DH)D-glucose. Preferred alternative substrates for D-glucose are those for which, relative to the specificity between Glucose-6-phosphate (G-6-P) and G-6-P-DH, the rate of reaction between the enzyme G-6-P-DH and the selected substrate is less than 50%, more preferably less than 10% and most preferably less than 5%.

One preferred alternative to the use of D-Glucose/G-6-P-DH is the use of Glucose Dehydrogenase (GLD) according to the following reaction wherein D-Glucose is the 100% reactive substrate:

If glucose dehydrogenase is used as the enzyme, preferred substrates for reduction of the NAD coenzyme and their relative degree of cross reactivity when compared to D-Glucose are:

| Substrate | Relative Activity |
|---|---|
| xylose | 8.9% |
| L-sorbose | 0.3% |
| D-mannose | 2.4% |
| D-fructose | 0.8% |
| D-galactose | 0.1% |
| D-lactose | 1.2% |
| D-sorbitol | 0.1% |
| inositol | 0.2% |
| maltose | 3.9% | wherein the figures in brackets represent the rate of reaction relative to that of Glucose-dehydrogenase 1β-D-glucose with 1β-D-glucose.

Alternatively, using Glycerol Dehydrogenase (GLY.DH) as the enzyme, suitable substrates in the reaction

and their activity relative to glycerol (100%) are

| Substrate | Relative Activity |
|---|---|
| Glycerol-α-monochlorohydrin | 48.5% |
| Ethylene glycol | 7.8% |
| 2,3-Butanediol | 52.6% |

Wherein Leucine Dehydrogenase (L.D) is used as the enzyme according to the reaction

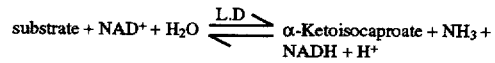

suitable substrates and their activity relative to L-leucine (100%) are

| Substrate | Relative Activity |
|---|---|
| L-Valine | 74% |
| L-Isoleucine | 58% |
| L-Norvaline | 41% |
| L-Norleucine | 10% |
| L-Methionine | 0.6% |
| L-Cysteine | 0.3% |

If L-Alanine Dehydrogenase (A.D) is used as the enzyme in a reaction system similar to that used for Leucine Dehydrogenase, a suitable substrate and its activity relative to L-alanine (100%) is

| Substrate | Relative Activity |
|---|---|
| L-serine | 5% |

3α-Hydroxysteroid Dehydrogenase (H.DH) may also be used as an enzyme in combination with the substrates listed below. Their activities relative to Cholic Acid are also listed.

| Substrate | Relative Activity |
|---|---|
| Lithocholic Acid | 96% |
| Etiocholic Acid | 60% |

Wherein, L-Lactate Dehydrogenase (LDH) from Lactobacillus sp. is used as the enzyme in the following reaction,

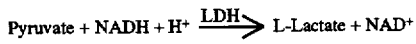

Pyruvate + NADH + H⁺ —LDH→ L-Lactate + NAD⁺ suitable substrates and their activity relative to L-Lactate are:

| Substrate | Relative Activity |
|---|---|
| 2-oxoglutarate | 0.09% |
| Oxoloacetate | 36% |

Wherein NADP is the coenzyme, for example from Yeast, preferred substrate/enzyme combinations are:

| | |
|---|---|
| G-6-P—DH/galactose-6-P | 25% |
| G-6-P—DH/2-deoxyglucose-6-P | 18% |
| G-6-P—DH/glucosamine-6-P | 2% |

The figures in on the right hand side represent the relative reactivity to that of a G-6-P-DH/G-6-P pair.

It is also possible using NADP as coenzyme to combine as enzyme/substrate glycerol-3-phosphate dehydrogenase with dihydroxy acetone phosphate.

As described in the preamble to this specification, the other requirements of a reagent according to the invention for use in the determination of serum bicarbonate levels are phosphoenol pyruvate (PEP), phosphoenol pyruvate carboxylase (PEPC), nicotinamide-adenine dinucleotide, reduced (NADH) and malate dehydrogenase(MDH).

Levels of PEP must be selected such that optimum performance of the reagent is achieved. This may vary according to the other components of the reagent selected, however, it has been found that a concentration in the range 1.5 mmol/L to at least 15 mmol/L is suitable in the context of this invention. Below 1.5 mmol/L substrate depletion occurs thereby affecting the stability of the reagent. Different salts of PEP may be used without compromising the stability of the reagent. It should be noted that the higher the level of PEP, the lower the pH of the reagent becomes. Thus buffer levels may need to be adjusted to achieve the optimum pH level.

The level of coenzyme in the reagent will vary according to the following factors:
linearity required in measurement
wavelength chosen
sample to reagent volume ratio
photometric system of the analyzer selected.

In general, increasing the sample volume improves the sensitvity but decreases the linearity of the reading obtained, whereas decreasing the sample volume improves linearity at the expense of losing sensitivity.

The preferred wavelength of measurement is 320–400 nm, however, the level of coenzyme used should be adjusted so that the absorbance preferably does not exceed 2.0 A. The preferred wavelength of absorbance according to the invention is 380 nm.

The level of PEPC is preferably selected so that the end point reaction is achieved within the desired time frame. For example, if a desired completion time is 5 minutes at 37° with a 50 mmol sample, a level of at least 380 U/L may be selected. Preferably the PEPC is obtained from a microbial source so as to reduce the risk of endogenous contamination of the reagent.

MDH is also preferably obtained from microbial sources so as to limit the risk of endogenous contamination. Appropriate levels are in the range 150–1500 U/L, more preferably 200–400 U/L.

The reagent according to the invention may include in addition to the coenzyme reduction system and other essential substrates and enzymes necessary to determine the analyte concentration, preservatives, chelating agents, surface active agents, protease inhibitors, buffers, cofactors, LDH inhibitors, antibacterials and other constituents which perform stability enhancing functions but do not materially affect the characteristics of the invention.

The primary criteria for selecting a buffer is such that it will have good buffering capacity at the selected pH with minimal binding of divalent cation. A general rule of thumb is that a buffer may be considered effective if its pKa is ±1.0 pH units from the chosen pH. A preferred pH of the reagent according to the invention is 7–9, more preferably 8.0 at 20° C. At this preferred pH a compromise is reached between optimum enzyme activity and the stability of the enzymes and coenzyme in solution. A lower pH may result in increased degradation of the coenzyme.

Suitable buffers are HEPES, 4-morpholine propanesulfonic acid (MOPS) or 2-[tris(hydroxymethyl) methylamino]-1-ethane-sulfonic acid (TES) or the other GOOD buffers, TRICINE, BICINE, TEA and TAPS. Preferred buffers according to the invention are TRIS and/or HEPES having a total ionic strength preferably of 30–100 mmol/L, and more preferably approximately 58 mmol/L The sample to be tested may be diluted with any suitable diluent if desired, such as deionized water or saline.

Magnesium ions are required as cofactor in the PEPC reaction described elsewhere in this specification. A concentration of 4–20 mmol/L is suitable. Appropriate sources of magnesium ions include Magnesium Sulphate (anhydrous), Magnesium Chloride and Magnesium acetate as well as other suitable magnesium salts.

Preservatives such as sodium azide ($NaN_3$), hydroxybenzoic acid, gentamicin, Thymol and mercury-free preservatives available from Boehringer Mannheim are suitable. The appropriate level is such that the preservative retains its preservative properties for at least 6–8 months when stored at 2°–8° without inhibiting the enzymes present in the reagent. A suitable range fulfilling these criteria is 0.1–1.0 g/L.

Non-ionic surface active agents such as octyl phenoxypolyethoxy ethanol or a polyoxyethylene fatty alcohol ether are suitable. PMSF or Aprotinin are known protease inhibitors and, sodium oxamate, oxalic acid or gossypol will effectively inhibit interference due to Lactic Dehydrogenase. This last component may be required for patients having high levels of pyruvate since these cause interference in enzymatic bicarbonate reactions. A suitable level of for example, sodium oxomate is 1.0 g/L. Other suitable enzyme stabilizers include bovine serum albumin, bovine gamma globulin, N-acetyl cysteine and glycerol.

A variety of chelating agents such as EDTA, EGTA, N-(2-hydroxyethyl)-ethylenediaminetriacetic acid (HEDTA), etc. are also suitable. Suitable defoaming agents may also be added if desired.

In one preferred embodiment of the invention, the reagent essentially comprises

| | |
|---|---|
| G-6-P—DH | coenzyme reduction |
| D-glucose | system |
| PEP | substrate |
| PEPC | substrate specific |
| MDH | enzymes |
| NADH | coenzyme |

In addition, there is preferably included TRIS buffer, HEPES free acid, Sodium Oxamate, Sodium Azide, Bovine Serum Albumin and Magnesium Sulphate (anhydrous).

One reagent formulated in accordance with the invention is as follows:

| RAW MATERIAL | MOLECULAR WEIGHT | CONCENTRATION | QUANTITY/ LITER |
|---|---|---|---|
| TRIS Buffer | 21.14 | 40 mM | 3.5–5.5 g |
| HEPES free acid | 238.3 | 18 mM | 3.5–5.3 g |
| PEP-MCHA Salt | 267.1 | 6.0 mM | 1.0–2.2 g |
| Sodium Oxamate | 111.03 | 9 mM | 0.5–1.5 g |
| Sodium Azide | 65.01 | 7.7 mM | 0.25–0.75 g |
| Bovine Serum Albumin | 0.1% | | 0.5–1.5 g |
| NADH.Na$_2$3H$_2$O | 763.5 | 1.6 mM | 0.6–1.80 g |
| Magnesium Sulphate (anhydrous) | 120.4 | 8 mM | 0.5–1.3 g |
| D-Glucose | 180.16 | 0.25 mM | 40.0–50.0 g |
| G-6-PDH (Leuconostoc Mesenteroides) | | | 3000–4000 U |
| PEPC (microbial) | | | 380–440 U |
| MDH (microbial) | | | 220–290 U |

In another aspect of the invention there is provided an improvement in an enzymatic method of determination of the concentration of serum bicarbonate in a sample body fluid wherein the degree of oxidation of a coenzyme is measured, the improvement comprising stabilizing a reagent comprising said coenzyme against oxidation by a coenzyme reduction system comprising an enzyme and substrate pair selected so as to enable continuous regeneration of said coenzyme throughout storage of said reagent.

In a preferred method according to this aspect of the invention, the enzyme of the enzyme and substrate pair has incomplete specificity for said substrate thereby reducing the rate of cross reactivity between enzyme and substrate.

In a preferred embodiment of this aspect of the invention, the coenzyme reduction system comprises an enzyme and substrate having a specificity for each other, relative to the specificity of the enzyme for its natural substrate, of less than 100%, preferably less than 50% and most conveniently less than 10%. Most conveniently, the specificity of the enzyme/substrate pair for each other, relative to the specifity of the enzyme for its natural substrate, is less than 5%, desirably approximately 2%.

The selection of coenzyme, substrate and enzyme may be made from those mentioned hereinabove in relation to the reagents of the invention, depending on the analyte to be assessed.

In one embodiment of this aspect of the invention, the preferred components of the coenzyme reduction system used for determination of total $CO_2$ concentration are NADH, G-6-P-DH and D-glucose such that the stabilization reaction taking place is

Due to the low specificity of G-6-P-DH for D-glucose this stabilization reaction is slow and thus not competitive with the main reactions

which take place upon addition of the sample body fluid.

EXAMPLE

The stability of one particular $CO_2$ reagent formulated in accordance with the invention was tested as follows:

| FORMULATION: | |
|---|---|
| TRIS Buffer | 4.86 g/L |
| HEPES free acid | 4.31 g/L |
| PEP - MCHA Salt | 1.60 g/L |
| Sodium Oxamate | 1.00 g/L |
| Sodium Azide | 0.50 g/L |
| Bovine Serum Albumin | 1.00 g/L |
| NADH.Na$_2$3H$_2$O | 1.20 g/L |
| Magnesium Sulphate (anhydrous) | 0.96 g/L |
| D-Glucose | 45.04 g/L |
| G-6-PDH (*L. Mesenteroides*) | 3500 U/L |
| PEPC (microbial) | 410 U/L |
| MDH (microbial) | 250 U/L |

Optimum levels of D-glucose and G-6-PDH were determined by testing the rate of regeneration of NADH with varying levels of D-glucose and G-6-PDH. The rate of regeneration of NADH from NAD+ is proportional to the amount of enzyme G-6-PDH and to a lesser extent the level of D-glucose. 2 ml aliquots of bicarbonate formulation containing 250 U/L MDH, 400 U/L PEPC, 6 mmol/L PEP and 50 mmol/L D-glucose at pH 8.0 were added to cuvettes and spiked with 20 µl of a 50 mmol/L bicarbonate sample. The cuvettes were then sealed with parafilm to prevent further $CO_2$ contamination, and the time course for NADH regeneration monitored at 380 nm and at 25° C. in a Shimadzu spectrophotometer over a 48 hour period. It was determined from these results that it was preferable to use 250 mmol/L of D-glucose as less G-6-PDH was used to obtain a similar rate of regeneration. The optimum level of G-6-PDH was determined to be in the range 2.5–5.0 KU/L since it did not effect the main reaction giving a stable end-point. A level of 3.5 KU/L of G-6-PDH was selected since this gave an acceptable regeneration rate of NADH over 6 months when the reagent was stored at 4° C. capped. An acceptable regeneration rate is considered to be in the range 0.10–0.90mAbs/min at 20°–25° C.

STORAGE CONDITIONS:

capped and refrigerated (2°–8° C.)

| SPECTROPHOTOMETRIC PARAMETERS (Shimadzu PC2101): | |
|---|---|
| reaction temperature | 37° C. |
| reagent to sample volume | 100:1 |
| wavelength | 380 nm |
| cuvette path length | 1 cm |

These spectrophotometric parameters were used to determine the following

Initial absorbance of reagent at 380 nm  
Reagent Blank rate at 380 nm  
reaction ΔAbsorbance completion time at 37° C.  } 50 mmol/L standard used to check  
regeneration rate at 20° C. (expressed in mAbs/min)

The following results were obtained:

| storage at 2–8° C. (weeks) | 6 | 9 | 12 | 16 | 21 | 24 | 28 | fresh reagent |
|---|---|---|---|---|---|---|---|---|
| Initial absorbance | 1.81 | 1.83 | 1.76 | 1.69 | 1.65 | 1.61 | 1.56 | 1.68 |
| Blank rate (ΔAbs/10 min) | 0.02 | 0.01 | 0.01 | 0.01 | 0.01 | 0.01 | 0.01 | 0.01 |
| completion time (min) | 4' | 4' | 5' | 5' | 5' | 5' | 5' | 4' |
| ΔAbsorbance | 0.67 | 0.7 | 0.69 | 0.68 | — | 0.68 | 0.7 | 0.68 |
| regeneration rate | 0.41 | 0.38 | 0.35 | 0.31 | 0.28 | 0.25 | 0.2 | 0.47 |

CORRELATION STUDIES:

Bicarbonate levels were determined on patient sera using fresh reagent, reagent stored for 6 months at 2°–8° C., and fresh regular reagent)not including the regeneration system). Results (mmol/L) were as follows:

| Regular fresh reagent | regeneration technology (6 months old) | regeneration technology (fresh) |
|---|---|---|
| 0 | 0 | 0 |
| 15 | 17 | 15 |
| 20 | 22 | 20 |
| 21 | 22 | 21 |
| 22 | 23 | 22 |
| 23 | 25 | 23 |
| 23 | 24 | 22 |
| 23 | 24 | 23 |
| 24 | 26 | 24 |
| 24 | 24 | 23 |
| 28 | 29 | 27 |
| 28 | 29 | 28 |
| 28 | 29 | 28 |
| 29 | 32 | 30 |
| 29 | 29 | 28 |
| 30 | 31 | 30 |
| 30 | 32 | 30 |
| 30 | 31 | 30 |
| 31 | 32 | 30 |
| 33 | 34 | 33 |
| 33 | 33 | 33 |
| 33 | 33 | 33 |
| 35 | 36 | 35 |
| 35 | 36 | 36 |
| 36 | 37 | 36 |
| 37 | 38 | 37 |
| 39 | 40 | 39 |
| 40 | 41 | 40 |
| 44 | 44 | 44 |
| 44 | 45 | 44 |
| 29 | 30 | 29 |

From the results presented it is evident that the regeneration $CO_2$ reagent is exhibiting at least 6–7 months stability when stored capped at 2°–8° C. The reagent must have an initial absorbance of 1.0 A to be functional. After 7 months the reagent still has an absorbance of at least 1.5 A. The completion time has hardly shifted at 4–5 minutes as has the sensitivity which has remained at 0.67–0.70 A over the testing period, indicating good calibration stability. Studies of Linearity indicate that linearity is retained at at least 40 mmol/L in both the fresh reagent and in a 28 week old sample.

The patient correlation data provides further evidence that there is no significant difference in performance when comparing fresh reagent versus reagent stored at 2°–8° C. for 6 months ($r^2=0.997$).

The incorporation of the regeneration system according to the invention has resulted in an increase in reconstituted stability of a serum bicarbonate measurement capped reagent from 1 month at 2°–8° C. to at least 6–8 months at 2–8° C. The stability of uncapped reagents has increased from one day at room temperature (18°–25° C.) to approximately 7 days at room temperature. Other major advantages of the reagent and method according to the invention are that the reagent is a single vial reagent thereby reducing space and inventory problems associated with prior art reagents, and that it is adaptable to varying instrumentation systems.

It should be appreciated that there are numerous substrate/enzyme "unnatural" pairs which may be used to slow the regeneration of the coenzyme used in the reagent and method of the invention. In addition to those mentioned herein, there are others which are not commercially available or which are prohibitively expensive.

I claim:

1. A reagent for enzymatic determination of the concentration of serum bicarbonate levels in a patient wherein the degree of oxidation of a coenzyme is measured, said reagent being stabilized against oxidation by a coenzyme reduction system comprising an enzyme and substrate pair selected so as to enable continuous regeneration of said coenzyme throughout storage of said reagent, said enzyme having incomplete specificity for said substrate.

2. The reagent of claim 1 wherein said enzyme is derived from a microbial source.

3. The reagent of claim 1 wherein said continuous regeneration occurs at a rate from 0.10 to 0.90 mAbs/min at temperature from 20° to 25° C.

4. The reagent of claim 1 wherein said enzyme substrate pair is glucose-6-phosphate dehydrogenase/D-glucose.

5. The reagent of claim 1 which is configured as a single vial.

6. A reagent as claimed in claim 1 wherein the degree of specificity between said enzyme and said substrate is less than 50% on an equimolar basis.

7. A reagent as claimed in claim 1 wherein the degree of specificity between said enzyme and said substrate is less than 10% on an equimolar basis.

8. A reagent for enzymatic determination of the concentration of serum bicarbonate levels in a biological sample from a patient wherein the degree of oxidation of a coenzyme is measured, said reagent being configured as a single vial and being stabilized against oxidation by a coenzyme reduction system comprising an enzyme and substrate pair selected so as to enable continuous regeneration of said coenzyme throughout storage of said reagent.

9. The reagent of claim 8 wherein said coenzyme reduction system comprises an enzyme and a substrate, said enzyme having incomplete specificity for said substrate.

10. The reagent of claim 9 wherein the degree of specificity between said enzyme and said substrate is less than 50% on an equimolar basis.

11. The reagent of claim 9 wherein the degree of specificity between said enzyme and said substrate is less than 10% on an equimolar basis.

12. The reagent as claimed in claim 9 wherein said continuous regeneration occurs at a rate in the range of 0.10–0.90 mAbs/min at 20°–25° C.

13. The reagent as claimed in claim 8 wherein said enzyme is derived from a microbial source.

14. The reagent as claimed in claim 8 wherein said enzyme/substrate pair is Glucose-6-Phosphate Dehydrogenase/D-glucose.

15. An improved enzymatic method for determination of the concentration of serum bicarbonate in a sample of a body fluid, said method comprising the step of measuring the degree of oxidation of a coenzyme, wherein the improvement in said method comprises stabilizing a reagent comprising said coenzyme against oxidation by use of a coenzyme reduction system, said coenzyme reduction system comprising an enzyme and substrate pair selected so as to enable continuous regeneration of said coenzyme throughout storage of said reagent, said enzyme having incomplete specificity for said substrate.

16. The improvement as claimed in claim 15 wherein said continuous regeneration occurs at a rate in the range of 0.10–0.90 mAbs/min at 20°–25° C.

17. The improvement as claimed in claim 15 wherein said enzyme is derived from a microbial source.

18. The improvement as claimed in claim 15 wherein said enzyme/substrate pair is Glucose-6-Phosphate Dehydrogenase/D-glucose.

19. The improvement as claimed in claim 15 wherein the degree of specificity between said enzyme and said substrate is less than 50% on an equimolar basis.

20. The improvement as claimed in claim 15 wherein the degree of specificity between said enzyme and said substrate is less than 10% on an equimolar basis.

21. The improvement as claimed in claim 15 wherein said reagent is configured as a single vial.

22. The reagent as claimed in claim 21 comprising 3,000–4,000 U/L Glucose-6-Phosphate Dehydrogenase, 40–50 g/L D-glucose, 1.0–2.1 g/L phosphoenolpyruvate, 300–1,300 U/L phosphoenolpyruvate carboxylase, 220–300 U/L Malate dehydrogenase and 0.6–1.80 grams reduced nicotinamide adenine dinucleotide.

23. A reagent for enzymatic determination of the concentration of serum bicarbonate levels in a patient wherein the degree of oxidation of a coenzyme is measured, said reagent comprising Glucose-6-Phosphate Dehydrogenase, D-glucose, phosphoenolpyruvate, phosphoenolpyruvate carboxylase, malate dehydrogenase and reduced nicotinamide adenine dinucleotide.

* * * * *